United States Patent [19]

Molteni et al.

[11] Patent Number: 5,083,920
[45] Date of Patent: Jan. 28, 1992

[54] PHANTOM FOR A DENTAL PANORAMIC X-RAY APPARATUS

[75] Inventors: Roberto Molteni; Vincenzo Di Piero, both of Milan, Italy

[73] Assignee: U.S. Philips Corporation, New York, N.Y.

[21] Appl. No.: 536,902

[22] Filed: Jun. 12, 1990

[30] Foreign Application Priority Data

Jun. 27, 1989 [EP] European Pat. Off. .......... 89201686

[51] Int. Cl.⁵ .................... A61C 19/04; G01D 18/00
[52] U.S. Cl. ........................................ 433/72; 378/207
[58] Field of Search ................ 433/72, 102, 224; 378/207

[56] References Cited

U.S. PATENT DOCUMENTS

| | | | |
|---|---|---|---|
| 3,878,611 | 4/1975 | Seaman | 433/72 |
| 4,126,789 | 11/1978 | Vogl et al. | 378/207 X |
| 4,472,829 | 9/1984 | Riederer et al. | 378/207 |
| 4,571,180 | 2/1986 | Kulick | 433/72 |
| 4,638,502 | 1/1987 | Yaffe | 378/207 |
| 4,649,561 | 3/1987 | Arnold | 378/207 |
| 4,663,772 | 5/1987 | Mattson et al. | 378/207 X |
| 4,788,706 | 11/1988 | Jacobson | 378/207 |
| 4,794,631 | 12/1988 | Ridge | 378/207 |
| 4,873,707 | 10/1989 | Robertson | 378/207 X |

FOREIGN PATENT DOCUMENTS

1-192348 8/1989 Japan ........................... 433/72

Primary Examiner—Robert P. Swiatek
Assistant Examiner—Nicholas D. Lucchesi
Attorney, Agent, or Firm—William Squire

[57] ABSTRACT

X-ray absorbing elongated segments are arranged with their midpoints registered along a standard jaw curve on an X-ray transparent holder. This holder is provided with locating pins and holes to ensure an exact positioning of the holder in the X-ray apparatus ensuring exact coincidence of the standard jaw curve thereof with the location of the dentition of patients to be examined.

20 Claims, 2 Drawing Sheets

PHANTOM FOR A DENTAL PANORAMIC X-RAY APPARATUS

FIELD OF THE INVENTION

BACKGROUND OF THE INVENTION

The invention relates to a test phantom for a dental panoramic X-ray apparatus.

Test phantoms are used in dental panoramic X-ray radiography for an objective assesment of image quality. In conventional radiography these kind of phantoms exist for many years. The kind of information supplied therewith refers mostly to the performances of the detector, viz film, screen and developing system. In fact, manufacturers of such apparatus normally offer their own quality phantoms and criteria.

In tomography and similar techniques, however, the movement system and the generator are relevant to the overall image quality. The relevant test phantoms become more complex and expensive, due to the increasing number of parameters determining image quality such as layer depth, positioning, movement artifacts, etc.

In dental panoramic radiography some additional and particular requirements complicate the matter further. In order to be of practical advantage to a large number of potential users, including private dentists, for instance in the framework of a program for quality assurance in dental practice, a test phantom should be inexpensive and data revealed therewith should introduce an easy and unambiguous interpretation. Available test phantoms are only suitable for certain subjective checks on particular models of equipment.

Further, the subtle but fundamental question arises of what exactly is the radiological target. Dental panoramic radiology exclusively depicts teeth and jaws; in order to acertain, by a technical test phantom, how closely the radiological projection modality conforms to the organ to be depicted, it is necessary to establish an objective, i.e. mathematical, model of the organ itself.

From studies for such a model it can be concluded that:

Sex, race and age play no substantial role in determining the average contour of the dental arch at roots level.

Individual deviations from the average curve are well within the range of a minimum unsharpness layer as provided by most rotational panoramic systems.

The average arrangement of roots in mandible and maxilla can be described by a simple even-terms polynomial equation.

It can be concluded that, in spite of considerable individual variations, it is possible to establish a meaningful model of the dentition, also including the average position and orientation of the Temporo Mandibular Joint (TMJ) condyles, on the basis of experimental statistical data available in literature.

Such a special technical test phantom would be useful for objective assesment of image quality, and of its congruency during the time, in dental panoramic radiograms, obtained from different equipment, from different units of the same type, and in different operating conditions.

Such a phantom should fulfill the following requirements:

To be based upon objective statistical data about the morphology of the dento-maxillo-facial complex, and to be applicable irrespective of sex, race and age.

To permit quantitave evaluation of the most important parameters affecting image quality and related to the dental panoramic equipment itself.

To be of simple and repeatable construction, and affordable cost, for widespread use in everyday dental practice.

Such a phantom should also be utilizable to check and optimize the performances of a dental X-ray panoramic apparatus during the progress of the design and application process, by optimizing the projection movement as a function of image quality obtained in the software-driven system.

SUMMARY OF THE INVENTION

To meet the above requirements a test phantom for a dental panoramic X-ray apparatus of the kind set forth in accordance with the invention comprises an array of strip shaped X-ray absorbing segments, the mid points of which are arranged corresponding to a standard jaw curve.

Such a phantom enables registration of the relevent parameters involved in image quality. Symmetry can easily be evaluated by comparing the two halves of an image formed, the halves being mirror images.

In principle the phantom comprises an array of thin metallic segments, of the same length and equally spaced, whose midpoints are arranged along a standard jaw curve.

The segments are registered in planes locally perpendicular to the standard jaw curve, and are inclined at 45 degrees with respect to the curve itself.

The phantom is intended to be positioned horizontally within the panoramic rotational equipment to be tested, in the position where the patient dentition is to lay, with the standard curve laying in the occlusal plane and its frontmost point on a few mm, for instance 7 mm, behind the incisors occlusion, to account for the distance of the midpoint of incisors roots.

The angle of incidance of the X-ray beam with respect to the standard jaw curve can be simply derived from the angle between the (horizontal) projection of the midline curve itself and the segments.

The horizontal magnification in any point is simply calculated by the ratio of the distance between two adjacent segments measured on the radiogram and the real distance on the test phantom.

In a preferred embodiment the segments are registered on mutually equal distances along a standard jaw curve and preferably are of equal length, facilitating image interpretation.

In a further embodiment the segments are inclined over about 45° with respect to the mid point jaw curve corresponding to the angle of incidence of the X-ray beam with respect to the standard jaw curve, this is the angle between the projection of the mid-line curve itself and the segments.

In a preferred embodiment the absorbing segments comprise a high atomic number element deposited on a flexible low X-ray absorbing support by any deposition technique such as vapour deposition, photo etching, printing or spraying. Preferably the support is a flexible strip being shaped to enable it to be fixed onto a mold of low X-ray absorbing material on which a jaw shaped surface is provided.

To obtain information from beyond the terminals of the jaw curve, additional segments can be introduced on the mold symmetrically with respect to both terminals of the jaw curve.

BRIEF DESCRIPTION OF THE DRAWING

Some embodiments in accordance with the invention will be described hereinafter with reference to the drawing wherein.

DESCRIPTION OF THE PREFERRED EMBODIMENT

Figure 1:
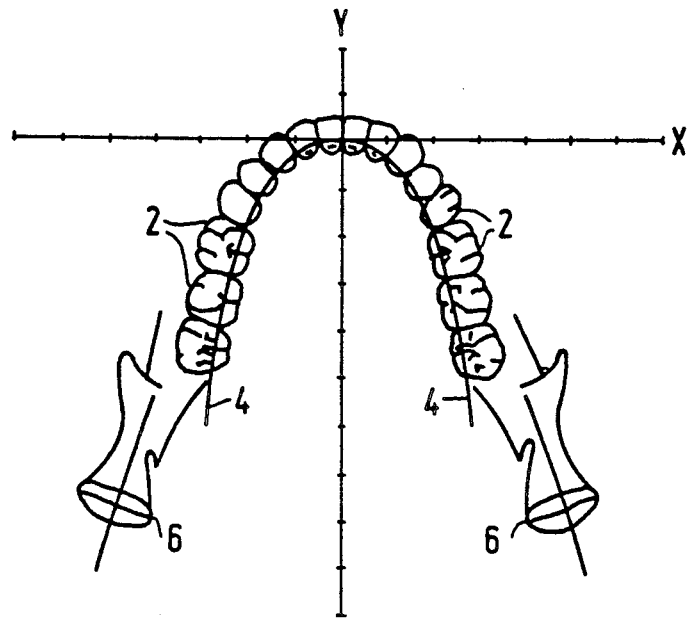
FIG. 1 is an example of an object to be examined.

The aim of an apparatus for dental panoramic radiography is to image a set of teeth 2 (FIG. 1) which are automatically arranged along a jaw curve 4 which curve is relatively uniform for men. That is, a relatively large portion of the jaw curves of adult persons show only relatively small deviations from a standard jaw curve which defines X and Y axes. Such a standard jaw curve thus can be defined by elements lying on the curve and by measuring the X- and Y-values of each element along the indicated X- and Y- axes for a large number of definitions. A standard jaw curve is symmetrical with respect to the Y-axis as occurs with the jaw curves of men. In normal practice, the location of the teeth with respect to the TMJ condyle 6 should be determinable. Preferably a phantom is created with this data.

Figure 2:
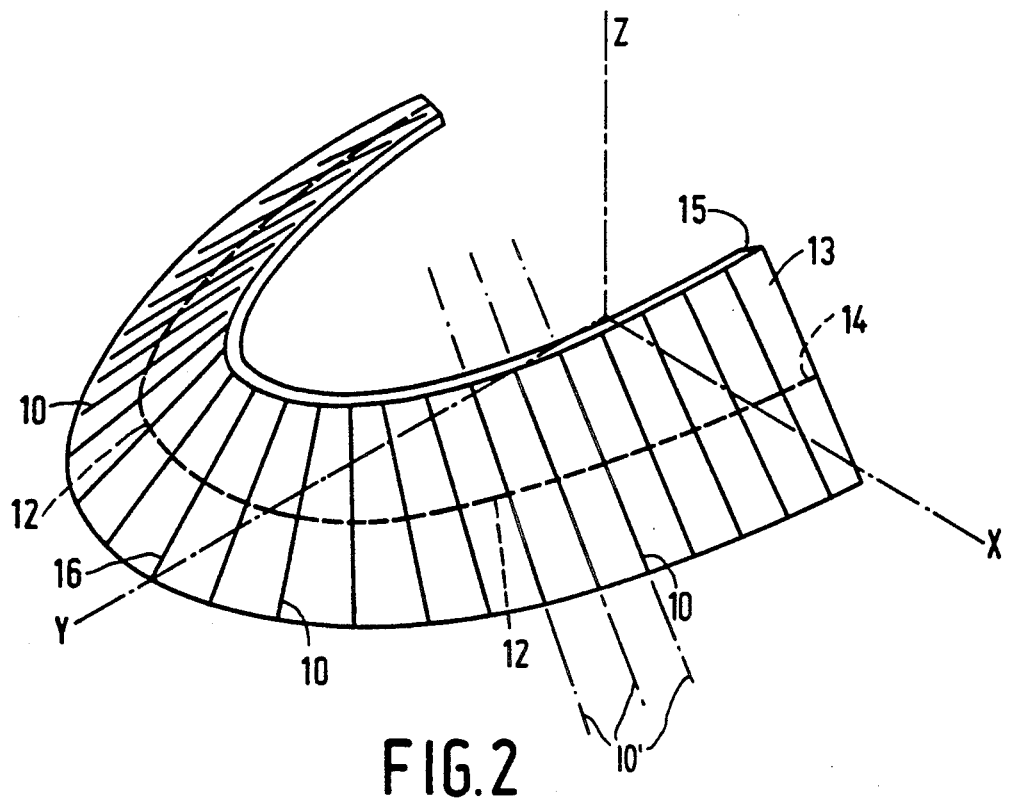
FIG. 2 is an arrangement of segments of a phantom according to an embodiment of the invention.

A geometrical registration of phantom linear segments 10 of a phantom in accordance with an embodiment of the invention is given in FIG. 2. Midpoints 12 of the segments 10 are oriented longitudinal along a standard jaw curve 14 lying in the X-Y plane. The segments 10 axes 10' are normal to the standard jaw curve and are inclined at an angle of about 45° with respect to the X-Y plane defined by curve 14 (and midpoints 12). The segments 10, for example 0.2 mm wide and about 10 mm long, are produced for example by a photolithographic etching process in a metal layer, preferably of copper, having a thickness of, for example, 10 µm. The metal layer is fixed on a surface 13 of an X-ray transparent or substantially transparent support 15, having for example, a thickness up to for example 250 µm. In order to keep the arrangement readable, the segments 10 are line segments. That is, the segments 10 are relatively narrow in transverse cross section as compared to their length as shown. The absorption of a copper layer may be increased by deposition of tin, lead, tin-lead alloy or any other applicable high X-ray absorbing material thereupon. The embodiment shows 25 segments for dentition control. No segments for TMJ imaging control are indicated in the embodiment shown but can be added thereto in other implementations.

Figure 3:
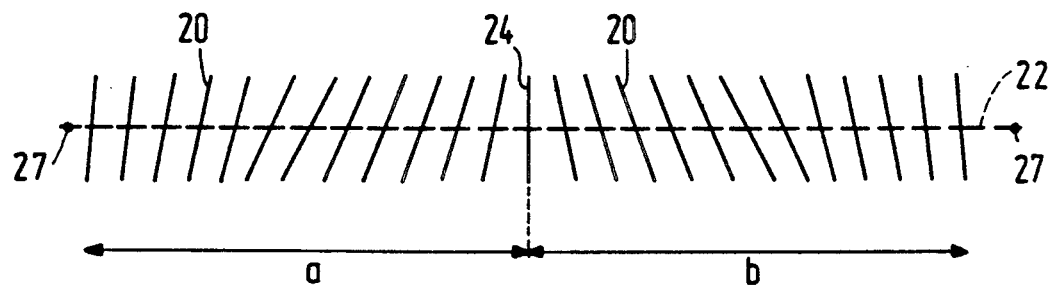
FIG. 3 is a radiographic image of the phantom of FIG. 2.

FIG. 3 shows an image of the phantom of FIG. 2 formed by X-ray radiation on an X-ray film sheet, for example. Images 20 of the segments 10 are registered along a straight line 22. A central segment image 24 corresponding to a central segment 16 in FIG. 2 is normal to the line 22 and the line images of the segments are a mirror image with respect to the mid-line segment image 24 which serves as a reference position. From such a segment image arrangement all relevant parameters of the imaging system can be controlled by measuring the segment line angular deviations from image 24 relative to line spacing distances, line sharpness etc., in the image. The image being registered on a transparent sheet, such as an X-ray film sheet, for example with dark lines corresponding to the segments images, is also easily compared with a standard, distortion-free image so that discrepancies, due to system irregularities, can easily be determined and defined. It now can easily be checked whether distance −a equals distance b for each portion of the image relative to image 24. Fixed phantom points 27 along line 22 can be used to represent distances −a and b. Line 24 is perpendicular to line 22 within a given limitation, line 22 is straight and horizontal, the image pattern is centered about line 24 and the distances between adjacent segment images are equal in mirror image fashion relative to image 24.

Figure 4:
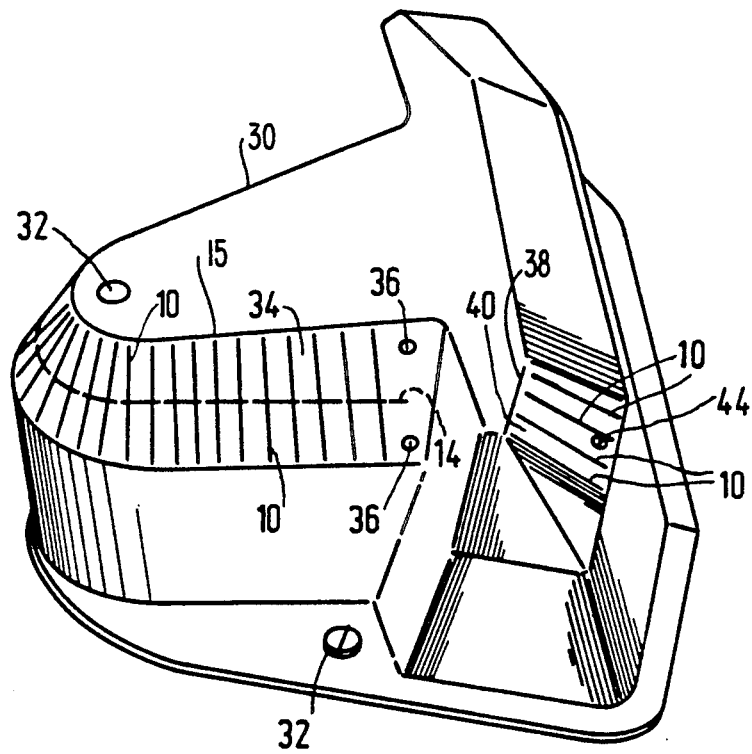
FIG. 4 is an example of a practical test phantom according to the embodiment of FIG. 2 fixed on an adapted holder.

FIG. 4 shows an example of a practical phantom device comprising a holder 30 which is easily attached to a radiographic apparatus with the aid of attachment elements 32, such as mating pins and holes. These attachment elements are preferably dimensioned and located to ensure an exact positioning of the phantom device in the apparatus so as to secure in a fixed portion the standard jaw curve thereof in coincidence with the jaw curve location of a dentition of a patient to be examined. The holder 30 is preferably made of a synthetic material, such as plastics or any other applicable X-ray transparent or substantially transparent material.

The holder 30 has a curved plane surface 34 on which the segments 12 and their supports sheet 15 are secured. Positioning elements 36 such as screws are added coinciding with holes in the support sheet 15 for example to thus position the support to holder 30 on surface 34. The support sheet 15 can be secured on the holder in any known manner and preferably is secured to an inner surface thereof. For purposes of clarity of illustration, the bonding surface is located on the outside of the holder 30 in this embodiment. For examination of the condyles further support sheets 38 with segments 10 are mounted on surfaces 40 of the holder, the segments 10 and support sheets being accurately fixed on supports 38, preferably on a 45° relative orientation therebetween. The sheets with the segments can be fixed in any appropriate manner to the relevant holder 30 bonding surface with the aid of locating elements 44. The bonding surfaces of the holder 30 for receipt of mating segments and supports (not shown) are also preferably located at inner surfaces of the holder 30.

In a known way, an image is made of the phantom and subsequently an image is made of patient's teeth exactly positioned as much as possible with its jaw curve on the jaw curve of the phantom. Any deviation of the systems are eliminated by making the deviations the same for both images.

What is claimed is:

1. Test phantom for a dental panoramic x-ray apparatus for a standard jaw curve, said phantom comprising a low X-ray absorbing support and an array of strip shaped X-ray absorbing segments on the support, the mid-points of which segments are arranged on a curve corresponding to said standard jaw curve.

2. Test phantom as claimed in claim 1 wherein the absorbing segments are registered on mutually equal distances from a reference position along said curve corresponding to said standard jaw curve.

3. Test phantom as claimed in claim 2 wherein the absorbing segments are of mutually equal length.

4. Test phantom as claimed in claim 3 wherein the segments are inclined over about 45° with respect to the plane of the mid-point curve of the segments.

5. Test phantom as claimed in claim 3 wherein the absorbing segments are line shaped.

6. Test phantom as claimed in claim 2 wherein the segments are inclined over about 45° with respect to the plane of the mid-point curve of the segments.

7. Test phantom as claimed in claim 2 wherein the absorbing segments are line shaped.

8. Test phantom as claimed in claim 2 wherein the absorbing segments, comprising substantially of a high atomic number metal, are deposited on a flexible low X-ray absorbing support by photo etching, printing or spraying.

9. Test phantom as claimed in claim 8 wherein said support comprises a flexible strip for supporting the absorbing segments and fixed onto a mold of low X-ray absorbing material.

10. Test phantom as claimed in claim 2 wherein said support comprises a flexible strip for supporting the absorbing segments and fixed onto a mold of low X-ray absorbing material.

11. Test phantom as claimed in claim 1 wherein the absorbing segments are of mutually equal length.

12. Test phantom as claimed in claim 11 wherein the segments are inclined over about 45° with respect to the plane of the mid-point curve of the segments.

13. Test phantom as claimed in claim 11 wherein the absorbing segments, comprising substantially of a high atomic number metal, are deposited on a flexible low X-ray absorbing support by photo etching, printing or spraying.

14. Test phantom as claimed in claim 13 wherein said support comprises a flexible strip for supporting the absorbing segments and fixed onto a mold of low X-ray absorbing material.

15. Test phantom as claimed in claim 1, wherein the segments are inclined over about 45° with respect to the plane of the mid-point curve of the segments.

16. Test phantom as claimed in claim 1, wherein the absorbing segments are line shaped.

17. Test phantom as claimed in claim 1, wherein the absorbing segments, comprise substantially atomic number metal, deposited on a flexible low X-ray absorbing support by photo etching, printing or spray techniques.

18. Test phantom as claimed in claim 1, wherein said support comprises a flexible strip for supporting the absorbing segments and fixed onto a mold of low X-ray absorbing material.

19. Test phantom as claimed in claim 18, wherein the strip shaped flexible support is fixed on a jaw shaped surface of the mold.

20. Test phantom as claimed in claim 1 wherein two sets of sub-test segments are added symmetrically to the ends of the jaw curve.

* * * * *